United States Patent [19]

della Valle et al.

[11] Patent Number: 4,707,469

[45] Date of Patent: Nov. 17, 1987

[54] GANGLIOSIDES MIXTURE, USEFUL AS A THERAPEUTICAL TOOL FOR ELIMINATING PAINFUL EFFECTS OR PERIPHERAL NEUROPATHIES

[75] Inventors: Francesco della Valle, Padua; Aurelio Romeo, Rome; Silvana Lorenzi, Padua, all of Italy

[73] Assignee: Fidia, S.p.A., Abano Terme, Italy

[21] Appl. No.: 744,338

[22] Filed: Jun. 13, 1985

[30] Foreign Application Priority Data

Jun. 27, 1984 [IT] Italy .............................. 48491 A/84

[51] Int. Cl.$^4$ ............................................. A61K 31/70
[52] U.S. Cl. ........................................ 514/26; 514/28
[58] Field of Search .................................... 514/26, 28

[56] References Cited

FOREIGN PATENT DOCUMENTS 0145209 6/1985 European Pat. Off. .
0167449 6/1986 European Pat. Off. .

OTHER PUBLICATIONS

Chemical Abstracts, vol. 102, No. 9, No. 72705f (Mar. 4, 1985).
Chemical Abstracts, vol. 96, No. 23, No. 193351d (Jun. 7, 1982).

Primary Examiner—Stanley J. Friedman
Attorney, Agent, or Firm—Birch, Stewart, Kolasch & Birch

[57] ABSTRACT

A ganglioside mixture, comprised of the gangliosides $GM_1$, $GD_{1a}$, $GD_{1b}$ and $GT_{1b}$, has been found to possess significant analgesic or pain relieving activity. The mixture is, therefore, useful for treating pain due to various peripheral neuropathies and the mixture is more effective than the individual gangliosides which comprise the mixture.

10 Claims, No Drawings

GANGLIOSIDES MIXTURE, USEFUL AS A THERAPEUTICAL TOOL FOR ELIMINATING PAINFUL EFFECTS OR PERIPHERAL NEUROPATHIES

BACKGROUND AND FIELD OF THE INVENTION

The present invention relates to a specific composition comprised of a mixture of gangliosides which mixture has been found to possess important analgesic or pain relieving activity.

Gangliosides represent a family of complex glycolipid molecules which are natural components of cellular membranes, in particular of neuronal membranes. These components are implicated in neuronal development, differentiation and regeneration processes. Exogenously applied gangliosides will insert into neuronal membranes in a stable manner. This incorporation is associated with the activation of a membrane-bound enzyme system, ($Na^+$, $K^+$) ATPase whose activity is essential for nerve impulse conductivity. Ganglioside prepreparations have been shown to possess a reinnervation-stimulating activity due to enhanced nerve sprouting, an essential feature of muscular reinnervation processes and of restoration of synaptic contacts. Electrophysiological and functional evidence of early recovery, due to parenteral ganglioside treatment, from nerve damage has been obtained in several animal models, including sensory nerve function after nerve transection, cochlear impairment by noise, diabetic neuropathy in mutant diabetic mice and intoxication Gangliosides are acidic glycolipids belonging to the family of biological compounds called glycosphingolipids. They are composed of 4 basic structural units: a long-chain animoalcohol, a fatty acid, an oligosaccharide moiety and one or more sialosyl residues.

1. The long-chain aminoalcohol, present in brain gangliosides is identified as 4-sphingenine and its longer-chain analog as 4-eicosasphingenine; these compounds are commonly called sphingosines.

FIG. 1:
Structure of Sphingosines

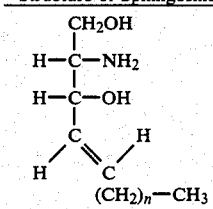

n = 12 4-spingenine
n = 14 4-eicosasphingenine

The corresponding saturated compounds (sphinganines) are also present in gangliosides in minor proportions.

2. A fatty acid is linked by means of an amide bond to the sphingosine base. In brain gangliosides this fatty acid is more than 95% accounted for by stearic acid (18:0). Other fatty acids are encountered in minor proportions, i.e. arachidic acid (20:0), palmitic acid (16:0) or palmitoleic acid (16:1Δ$^9$). The aminoalcohol plus the fatty acid form the unit termed ceramide, which represents the hydrophobic part of the ganglioside molecule.

3. The oligosaccharide chain linked to ceramide characterizes the large family of glycosphingolipids to which gangliosides belong. The spingolipids are classified in two subgroups, based on the carbohydrate immediately linked to ceramide. The first and smaller subgroup derives from galactosyl-ceramide.

Most of the glycosphingolipids, and thus virtually all gangliosides, belong to the subgroup derived from glucosyl-ceramide.

4. Sialic acid is present in brain gangliosides mainly in the N-acetyl form, but in some ganglioside species the N-glycolyl form has been identified. This residue is generally termed neuraminic acid (NANA or NGNA).

FIG. 2:
N—acetylneuraminic acid; open chain and hemiketalic ring.

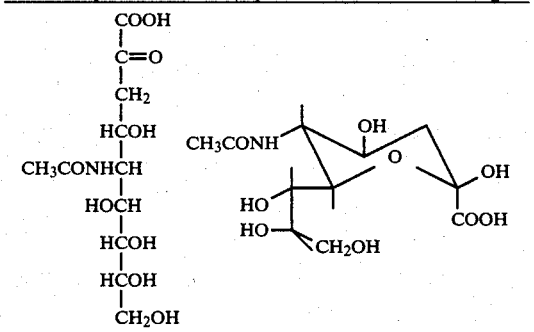

The hydrophilicity of gangliosides is due to the oligosaccharide chain and to the number of sialosyl residues linked to this chain.

Distribution of Gangliosides

The highest concentration of gangliosides is found in cerebral grey matter, which contains approximately 2.5 micromoles of NANA per gram wet weight (approximately 0.4% of dry weight, 0.6% of total lipids) (Ledeen R., Salsmar K., Cabrera M., J. Lipid Res.: 9, 129 (1968)).

About 90% of the total ganglioside content of mammalian brain is comprised of four gangliosides having an identical oligosaccharide sequence:

Gal β1→3GalNAc β1→4 Gal β1-4>Glc β1→1 Cer

Most of the remaining 10% mammalian brain ganglioside content is comprised of gangliosides lacking the terminal galactose or the galactosyl-Nacetylgalactosamine unit (Svennerholm L., Mansson S., Li Y., J. Biol. Chem. 248: 740 (1973)).

STRUCTURE AND NOMENCLATURE OF GANGLIOSIDES

Brain gangliosides have been isolated and purified by chromatographic procedures. The structure of ganglioside GM$_1$ was determined first and was shown to be common to the four main gangliosides present in mammalian brain. A summarizing structure description is given in Table 1, which is followed by detailed single descriptions of the four main mammalian brain gangliosides:

SUMMARIZING TABLE OF GANGLIOSIDE STRUCTURE

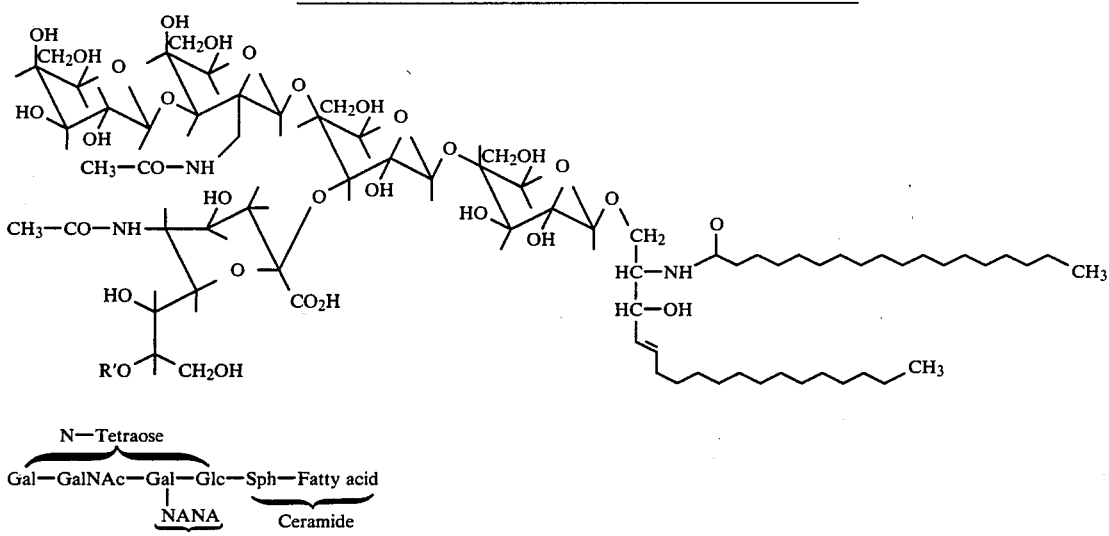

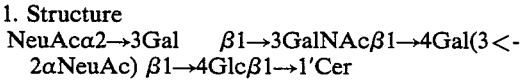

TABLE 1
Structures of Four Main Mammalian Brain Gangliosides

| Symbol according to Svennerholm* | Abbreviation according to IUPAC-IUB | R | R |
|---|---|---|---|
| $GM_1$ | $II^3\alpha$-NeuAc—GgOse$_4$Cer | H | H |
| $GD_{1a}$ | $II^3\alpha$-NeuAc—$IV^3$-$\alpha$-NeuAc—GgOse$_4$Cer | NANA | H |
| $GD_{1b}$ | $II^3\alpha$-(NeuAc)$_2$GgOse$_4$Cer | H | NANA |
| $GT_{1b}$ | $II^3\alpha$-(NeuAc)$_2$—$IV^3$-$\alpha$-NeuAc—GgOse$_4$Cer | NANA | NANA |

*(Svennerholm L., J. Neurochem. 10: 613 (1963))

1. Ganglioside $GM_1$

Ganglioside $GM_1$ has the simplest structure of the four main gangliosides; the others ($GD_{1a}$, $GD_{1b}$, $GT_{1b}$) are identical but for the addition of one or more sialosyl residues attached by glycosidic linkages to the oligosaccharide moiety.

1.1. Structure

Gal $\beta1\rightarrow$3GalNAc$\beta1\rightarrow$4 Gal(3<-2NeuAc)$\beta1\rightarrow$4Glc $\beta1\rightarrow$1'Cer Substituents on the root oligosaccharide are given at the beginning of the name by a Roman numeral that indicates the monosaccharide residue (counting from ceramide) on which the substituent is located. A superscript arabic numeral indicates the position of the glycosidic linkage.

1.2. Empirical formula (Kuhn R., Wiegandt H. (1963):

Chem. Ber. 96, 866)
$C_{13}H_{131}N_3O_{31}$ 1.3. Molecular weight 1536.9, calculated on the basis of 2 Gal, 1 Glc, 1 NANA, 1 GalNAc, 1 Sphingosine ($C_{18:1}$), 1 Stearic acid.

2. Ganglioside $GD_{1a}$ 2.1. Structure

NeuAc$\alpha2\rightarrow$3Gal $\beta1\rightarrow$3GalNAc$\beta1\rightarrow$4Gal(3<-2$\alpha$NeuAc) $\beta1\rightarrow$4Glc$\beta1\rightarrow$1'Cer 2.2. Empirical formula (Kuhn R., Wiegandt H. (1963):

Chem. Ber. 96, 866) $C_{84}H_{148}N_4O_{39}$ 2.3. Molecular weight 1838.0, calculated on the basis of 2 Gal, 1 Glc, 2 NANA, 1 GalNAc, 1 Sphingosine ($C_{18:1}$), 1 Stearic acid.

3. Ganglioside $GD_{1b}$ 3.1. Structure

Gal$\beta1\rightarrow$3GalNAc$\beta1\rightarrow$4 Gal(3<-2$\alpha$NeuAc8<-2$\alpha$NeuAc) $\beta1\rightarrow$4Glc$\beta1\rightarrow$1'Cer.

3.2. Empirical formula (Kuhn R., Wiegandt H. (1963):

Chem. Ber. 96, 866)
$C_{84}H_{148}N_4O_{39}$ 3.3. Molecular weight 1838.0, calculated on the basis of 2 Gal, 1 Glc, 2 NANA, 1 GalNAc, 1 Sphingosine ($C_{18:1}$), 1 Stearic acid.

4. Ganglioside $GT_{1b}$ 4.1. Structure

NeuAc$\alpha2\rightarrow$3Gal$\beta1\rightarrow$3GalNac$\beta1\rightarrow$4Gal(3<-2$\alpha$NeuAc8<-2$\alpha$NeuAc) $\beta1\rightarrow$4Glc$\beta1\rightarrow$1'Cer 4.2. Empirical formula (Kuhn R., Wiegandt H. (1963):

Chem. Ber. 96, 866)
$C_{95}H_{165}N_5O_{47}$ 4.3. Molecular weight 2129.4, calculated on the basis of 2 Gal, 3 NANA, 1 GalNAc, 1 Sphingosine ($C_{18:1}$), 1 Stearic acid.

It has now been found that a particular mixture of gangliosides provides both nerve reinnervation stimulating activity and analgesic activity. A specific ratio mixture of the gangliosides $GM_1$, $GD_{1a}$, $GD_{1b}$ and $GT_{1b}$ has been found to exhibit significant analgesic activity not previously known for such mixtures.

OBJECTS AND SUMMARY OF THE INVENTION

It is, therefore, one object of the present invention to provide a pharmaceutical composition comprised of a mixture of gangliosides which possess analgesic activity.

It is another object of the present invention to provide a pharmaceutical composition comprised of a mixture of the gangliosides $GM_1$, $GD_{1a}$, $GD_{1b}$ and $GT_{1b}$ in specific weight ratios such that the resultant mixture possesses analgesic activity greater than that for the individual components of the mixture.

It is a further object of the invention to provide a method for treating pain due to peripheral neuropathies by administering a composition comprised of a mixture of gangliosides, particularly a mixture of the gangliosides $GM_1$, $GD_{1a}$, $GD_{1b}$, and $GT_{1b}$.

These and other objects of the present invention are accomplished by producing a composition which is a mixture of the gangliosides $GM_1$, $GS_{1a}$, $GD_{1b}$ and $GT_{1b}$ in a specific weight ratio. This composition possesses significant analgesic activity and is useful for treating and relieving the pain due to various peripheral neuropathies.

DETAILED DESCRIPTION OF THE INVENTION

As discussed above, gangliosides represent a family of complex glycolipid molecules which are natural components of cellular membranes. Since gangliosides are mainly associated with neuronal membranes, it has been suggested (Fishman et al., Science, 194: 906-915) that they may play a role in the transfer of information across these membranes. Support for this suggestion has come from a series of observations implicating these molecules in a variety of cell-membrane mediated events, including neuronal development (Dimpfel W. et al., "Gangliosides in Neurological and Neuromuscular Function, Development and Repair". Eds. Repport and Gorio, Raven Press 119-134 (1981)), differentiation (Leon A. et al. (1981a) "Membranes in Growth & Development". Hoffman et al. 311-320, (1981)) and regeneration (Gorio A. et al. "Gangliosides in Neurological and Neuromuscular Function, Development and Repair". Eds. Rapport and Gorio, Raven Press 177-195).

A ganglioside mixture of the gangliosides $GM_1$, $GD_{1a}$, $GD_{1b}$ and $GT_{1b}$, purified for parenteral use, has been shown to possess a reinnervation-stimulating activity due to enhanced nerve sprouting (Gorio A. et al. Brain Res. 197: 236-241 (1980)). The nerve sprouting promoting activity has been confirmed both with in vitro neuronal tissue culture models (Roisen F. J. et al., Science, 214: 577-578 (1981); Hauw J. J. et al., Neurophysiologie. C.R. Acad. Sc. Paris, 292, . (8): 569-571 (1981)) and with in vivo animal denervation models (Gorio et al., Brain Res. 197, 236-241, 1980), Gorio et al. "Nervous System Regeneration, Birch Defects; original article series", 19, (u), 157-174, 1981).

The in vivo animal models (denervation of rat fast twitch muscle by crush of sciatic nerve, partial denervation of rat soleus muscle by resection and dislocation of L5 nerve root) have provided both electrophysiological and morphological evidence of enhanced collateral nerve sprouting, after treatment with exogenous gangliosides (5-50 mg/kg daily 1.p. injections), resulting in early functional recovery.

Electrophysiological and functional evidence of accelerated recovery from nerve damage due to ganglioside treatment has been described in several animal models, including sensory nerve function after nerve transection (Norido F. et al., Experientia, 37: 301-302 (1981); cochlear impairment by noise (Aporti F. et al., Nuovo Arch. Otol. Rinol. Laringol. 5, (1): 25-32 (1977); diabetic neuropathy in genetically diabetic neuropathy in genetically diabetic mice, (Norido F. et al. Muscle & Nerve); 5, 107-110 (1982)); intoxication with nerve damaging toxins, (Aporti F. et al.: Acta Otolaryngologica; 92, 433-437, (1981); Maroni M. et al. Clinical Toxicology 18, (12) 1475-1484 (1981).

On the basis of these experimental data the mixture of gangliosides $GM_1$, $GD_{1a}$, $GD_{1b}$, and $GT_{1b}$ is therapeutically indicated to be useful in a wide range of conditions of the peripheral nervous system where reinnervation may be stimulated and accelerated.

Such peripheral neuropathies include:

dysetabolic polyneuropathies (diabetic neuropathy, Pozza G. et al., "Gangliosides in Neurological and Neuromuscular Function, Development and Rapair". Eds. Rapport and Gario. Raven Press 253-258 (1981); Bassi S. et al., Muscle & Nerve, 5, 351-356 (1982); uremic neuropathy, Catizone L. et al., Clin. Terap., 85, (4): 395 (1978))

mechanical neuropathies (carpal tunnel syndrome, Trontelj J. V. et al., Effects of cerebral gangliosides in carpal tunnel syndrome (1981). Personal communication; compressive radiculopathy, Cubells J. M. et al., Med. clin. (Barcelona) 75, (4): 156-160 (1980); traumatic neuropathy, Gai A. M. et al., Europ. Medicophys., 16, (3): 221-231 (198)

Toxic neuropathies (iatrogenic neuropathy due to vincristine, Azzoni et al., Il Policlinico-Sez. Medica 85, (4), 255-262 (1978); alcoholic neuropathy, Mamoli B. et al, Europ. Neurol. 19: 320-326 (1980); Bassi S. et al., Electromyographic study of diabetic and alcoholic polyneuropathic patients treated with gangliosides. Muscle & Nerve, 5, 351-356 (1982))

miscellaneous neuropathies:

(Bell's palsy, Negrin M. et al., Min. Med., 69, (48): 3277-3282 (1978); Menieriform syndromes, Molino R. et al., Giorn. It. Ric. Clin. Terap., 2: 102-106 (1978); neurotrophic ulcers, Ferrandi C., Il Policlinico (Sez. Medica) 89, (3): 279-289 (1981))

METHOD OF PREPARATION

The individual ganglioside components comprising the composition of the invention can be extracted by various per se known procedures. For example, bovine brain cortex (nervous tissue) drawn from the animal is homogenized in phosphate buffer at pH 6.8. Six (6) volumes of tetrahydrofuran are then added and the resulting mixture is centrifuged. The supernatant or overfloating fraction is twice re-extracted with tetrahydrofuran. After centrifugation, the non-polar or apolar materials are removed by fractioning with ethyl ether and the aqueous tetrahydrofuran phase is introduced into an ion exchange column balanced with 50% ethanol. Ethanol (50%) is used as the eluent. To the effluent from the column is added barium hydroxide and four volumes of icy ethanol. After 18 hours under cold conditions, a precipitate is collected and then a slight amount of hydrochloric acid is added following solution in water. This solution is then dialized and lyophilized. The yield is now about 0.6 mg crude gangliosides per gram of nervous tissue being used.

The lyophilized powder is dispersed in 20 volumes chloroform-methanol (2:1); the solution is filtered to complete clearness and fractioned by adding 0.2 volumes potassium chloride solution in water (0.88%). The upper phase is separated, dialized and lyophilized. The final yield is about 0.3 mg gangliosides per gram of nervous tissue.

When separating the individual gangliosidic fractions, columns of silicic acid eluted with methanol-chloroform mixtures are utilized. Prior to use for human therapeutic application, assays should be carried out on the material obtained, such as assays relating to the absence of pyrogenic activity, proteins, anaphyllactogenic activity and histamine.

Pharmaceutical Compositions

For the novel therapeutic application according to the invention, a formulation of the ganglioside mixture should contain the individual gangliosides in the following ratios:

| Individual Gangliioside | Percent by Weight |
|---|---|
| $GM_1$ | about 19 to 23 |
| $GD_{1a}$ | about 36 to 44 |
| $GD_{1b}$ | about 14 to 18 |
| $GT_{1b}$ | about 17 to 21 |

In a particularly preferred formulation, the individual gangliosides are combined in the following weight ratio:

$GM_1$—21%
$GD_{1a}$—40%
$GD_{1b}$—16%
$GT_{1b}$—19%

It has also been found that the important pain relieving activity of the present invention can also be attained by administering the above gangliosides individually, as binary mixtures or a tertiary mixture. Thus any of the gangliosides can be administered as a single fraction or various compositions can be prepared combining any two or any three of the gangliosides. For example, GM and $GD_{1a}$, or GM and $GD_{1b}$ can be administered as binary mixtures.

In preparing a pharmaceutical composition according to the invention, the formulation should preferably contain a total $(GM_1+GD_{1a}+GD_{1b}+GT_{1b})$ ganglioside titer of $\geq 95.0\%$ (calculated with reference to dry weight). The preparations can be solutions of the ganglioside compounds or a lypholized powder of the compounds in association with one or more pharmaceutically acceptable carriers or diluents, and contained in buffered media at a suitable pH and isosmotic with physiological fluids. Each dose of the mixture will contain from about 10 to 100 mg of the ganglioside mixture or of the single ganglioside fractions or thier binary or tertiary mixtures thereof. The particular dosage will depend upon the desired effect and upon the administration route. For example, the dosage can be between 0.143 and 1.43 mg. of the active compounds per kg of body weight by day with a unitary dosage of between 10 and 100 mg/kg of body weight.

Some possible pharmaceutical compositions are as follows:

Preparation No. 1 - one ml vial contains:

| | | |
|---|---|---|
| ganglioside mixture of ratio: | | 100 mg |
| $GM_1$ | 21% | |
| $GD_{1a}$ | 40% | |
| $GD_{1b}$ | 16% | |
| $GT_{1b}$ | 19% | |
| phosphate buffer pH 7.6 M/100 in apyrogenic sterile bidistilled water | | q.s.a. 2 ml |

Preparation No. 2 - one 2 ml vial contains:

| | | |
|---|---|---|
| ganglioside mixture of ratio: | | 10 mg |
| $GM_1$ | 21% | |
| $GD_{1a}$ | 40% | |
| $GD_{1b}$ | 16% | |
| $GT_{1b}$ | 19% | |
| phosphate buffer pH 7.6 M/100 in apyrogenic sterile bidistilled water | | q.s.a. 2 ml |

Preparation No. 3 - one 2 ml vial contains:

| | | |
|---|---|---|
| ganglioside mixture of ratio: | | 25 mg |
| $GM_1$ | 25% | |
| $GD_{1a}$ | 40% | |
| $GD_{1b}$ | 16% | |
| $GT_{1b}$ | 19% | |
| Phosphate buffer pH 7.6 M/100 in apyrogenic sterile bidistilled water | | q.s.a. 2 ml |

Preparation No. 4 - one 2 ml vial contains:

| | | |
|---|---|---|
| ganglioside mixture of ratio: | | 75 mg |
| $GM_1$ | 25% | |
| $GD_{1a}$ | 40% | |
| $GD_{1b}$ | 16% | |
| $GT_{1b}$ | 19% | |
| phosphate buffer pH 7.6 M/100 in apyrogenic sterile bidistilled water | | q.s.a. 2 ml |

Preparation No. 5 - one 2 ml vial contains:

| | |
|---|---|
| monosialoganglioside $GM_1$ | 10 mg |
| phosphate buffer pH 7.6 M/100 in apyrogenic sterile bidistilled water | q.s.a. 2 ml |

Preparation No. 6 - one 2 ml vial contains:

| | |
|---|---|
| trisialoganglioside $(GT_{1b})$ | 10 mg |
| phosphate buffer pH 7.6 M/100 in apyrogenic sterile bidistilled water | q.s.a. 2 ml |

Preparation No. 7 - one 2 ml vial contains:

| | |
|---|---|
| a binary mixture of single fractions at the following ratio: | 30 mg |
| monosialoganglioside $GM_1$ 60% | |
| trisialoganglioside $GT_{1b}$ 40% | |
| phosphate buffer pH 7.6 M/100 in apyrogenic sterile bidistilled water | q.s.a. 2 ml |

Preparation No. 8 - one 2 ml vial contains:

| | |
|---|---|
| a binary mixture of single fractions at the following ratio: | 60 mg |
| monosialoganglioside $GM_1$ 45% | |
| trisialoganglioside $GT_{1b}$ 55% | |
| phosphate buffer pH 7.6 M/100 in apyrogenic sterile bidistilled water | q.s.a. 2 ml |

Preparation No. 9 - one 2 ml vial contains:

| | |
|---|---|
| one ternary mixture of single fractions at the following ratio: | 75 mg |
| monosialoganglioside $GM_1$ 30% | |
| disialogangliosides $(GD_{1a}$ or $GD_{1b})$ 45% | |
| phosphate buffer pH 7.6 M/100 in apyrogenic sterile bidistilled water | q.s.a. 2 ml |

Preparation No. 10 - each plaster contains:

| | |
|---|---|
| gangliosides | 100 mg |
| glycerine | 1.6 g |
| polyvinyl alcohol | 0.2 g |
| polyvinyl pyrrolidone | 0.1 g |
| excipient for increasing the intradermal penetration | 20 g |
| water | 1.5 g |

Preparation No. 11 - 100 g of cream contain:

| | |
|---|---|
| 4 gr of gangliosides in 5 gr of mixed liposomes of phospholipids polyethilenglicole monostearate | 15 g |
| glycerine | 1.5 g |
| sorbitol | 1.5 g |
| p-oxibenzoic acid esters | 0.125 g |
| water | 72.9 g |

Pharmalogical Properties

As discussed above, the ganglioside mixture composition, and the single fractions and the binary and tertiary mixtures thereof of the invention have been found to be useful for its analagesic activity in relieving pain due to various peripheral neuropathies. The following tests are conducted to show the improved and unexpectedly superior activity of the composition of the invention as compared to the individual component ganglioside compounds.

Relieving pain activity by procedure of writhing test with penylbenzoquinone in mouse The study was carried out using Swiss male mice (26-28g). The painful reaction induced by intraperitoneal injection of 0.25 ml/mouse of a 0.02% phenylquinone solution in 5% ethyl alcohol (writhing), was evaluated.

This injection determines a painful reaction which can be measured by the abdominal writhing of the animal.

The study evaluated the effect of the single ganglioside $GM_1$, $GD_{1a}$, $GD_{1b}$, and $GT_{1b}$ as well as the specific mixture of the invention described above in preparation No. 1 and abbreviated here as GA. Each ganglioside under examination and the mixture (GA) were administered by subcutaneous route 30 minutes before phenylquinone (solubilized in 10 ml/kg of distilled water).

The control animals received 10 ml/kg s.c. distilled water.

The number of writhes effected by each animal in a period of 5 minutes was evaluated (from the 5th to the 10th minute after injection of phenylquinone), thereby calculating the percentage of inhibition of the nervous reaction, compared to the controls.

Results of the writhing test

The results obtained are summarized in Table 2.

TABLE 2

Results of the Writhing Test with Intraperitoneal injection of 0.25 ml of a 0.25% phenylbenzoquinone solution in 5% ethyl alcohol.

| Treatment (S.C.) | Dose (mg/kg) | No. of animals | No. of writhes | inhibition percent |
|---|---|---|---|---|
| Control (water 10 ml/kg s.c.) | — | 60 | 39.9 ± 0.76 | — |
| GS | 1 | 6 | 30.3 ± 2.20 | 24.0 |
| | 2.5 | 6 | 17.9 ± 0.72 | 55.1 |
| | 5 | 6 | 13.0 ± 0.63 | 66.9 |
| | 10 | 12 | 11.9 ± 0.76 | 70.1 |
| | 20 | 6 | 16.6 ± 0.84 | 58.3 |
| | 30 | 6 | 16.8 ± 1.47 | 57.9 |
| | 50 | 6 | 26.8 ± 1.96 | 32.8 |
| $GM_1$ | 1 | 6 | 32.4 ± 1.98 | 18.7 |
| | 2.5 | 6 | 23.3 ± 1.40 | 41.6 |
| | 5 | 6 | 19.8 ± 0.60 | 50.3 |
| | 10 | 12 | 18.8 ± 1.28 | 52.8 |
| | 20 | 6 | 19.1 ± 0.89 | 52.1 |
| | 30 | 6 | 19.5 ± 0.43 | 51.1 |
| $GD_{1a}$ | 5 | 6 | 34.2 ± 0.32 | 14.2 |
| | 10 | 6 | 20.8 ± 1.38 | 47.8 |
| | 20 | 6 | 20.3 ± 1.12 | 49.1 |
| | 30 | 6 | 20.2 ± 1.08 | 49.3 |
| $GD_{1b}$ | 5 | 6 | 40.1 ± 0.86 | — |
| | 10 | 6 | 33.5 ± 1.43 | 16.0 |
| | 20 | 12 | 20.8 ± 0.54 | 47.8 |
| | 30 | 6 | 18.6 ± 1.09 | 53.3 |
| $GT_{1b}$ | 1 | 6 | 34.2 ± 0.68 | 14.2 |
| | 2.5 | 6 | 26.8 ± 1.06 | 32.8 |
| | 5 | 6 | 21.8 ± 0.81 | 46.6 |
| | 10 | 6 | 19.6 ± 1.12 | 50.8 |

TABLE 2-continued

Results of the Writhing Test with Intraperitoneal injection of 0.25 ml of a 0.25% phenylbenzoquinone solution in 5% ethyl alcohol.

| Treatment (S.C.) | Dose (mg/kg) | No. of animals | No. of writhes | inhibition percent |
|---|---|---|---|---|
| | 20 | 6 | 18.1 ± 1.35 | 54.6 |
| | 30 | 6 | 18.3 ± 1.20 | 54.1 |

From the data in Table 2, it can be seen that the analgesic activity of the ganglioside mixture (GA) and its single fractions has a dose-effect tendency. It was observed that the maximum effect was reached at the dose of 10 mg/kg, while at the higher doses (20-30 and 50 mg/kg) the activity gradually decreased, giving as a result, a bell-shaped dose-effect curve.

It was, moreover, shown that the analgesic activity of the individual gangliosides have the following relative activity, from highest to lowest activity:

$GA > GM_1 > GT_1 > GD_{1a} > GD_{1b}$

The maximum percentage of inhibition of writhing obtained with each individual ganglioside does not in any case exceed a maximum value of 55%. Indeed, the activity tends to become stable around the values reached with the dose of 10 mg/kg, without registering any significant increase in the analgesic response after further increases in the dose.

By extrapolating the data from the dose-effect curve, it is clear that the activity of the ganglioside mixture is the result of an interaction between the four associated gangliosides, characterized by a phenomena of synergism due to the specific ratio between the single fractions characterizing the total mixture of gangliosides, although the single fractions also demonstrated to have a good relieving pain activity.

Therapeutic Utilization

The above described experimental results evidence that the particular ganglioside mixture of the invention and its single fractions has significant analgesic or pain relieving activity. As a result, the ganglioside mixture, its single fractions, binary mixtures or tertiary mixtures thereof, is useful for relieving the pain caused by different peripheral neuropathies such as diabetic neuropathies, trigeminal neuralgia, sciatica, cervicobrachialgia, herpes zooster, post therapeutic neuropathies and other neuropathies with a serious high painful component.

For the treatment of the above pathologies, the gangliosides, either as the individual, binary, tertiary or quaternary mixtures, can be prepared in formulations such as ampoules, vials, plasters or creams duly prepared in combination with a pharmaceutically acceptable carrier, diluent or excipient.

These formulations, as appropriate, can be administered to a patient by various administration routes, including subcutaneous intramuscular, intravenous, topical, inuction, transcutaneous and transdermal. For example, the active ganglioside compounds can be formulated as a mixture with an appropriate excipient and prepared in a patch form, which is then applied directly to the skin, whereby the compounds pass through the skin into the patient.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for treating pain comprising administering to a host in pain a composition comprising an effective pain relieving amount of at least one ganglioside selected from the group consisting of $GM_1$, $GD_{1a}$, $GD_{1b}$ and $GT_{1b}$.

2. A method as in claim 1, wherein said composition comprises by weight, about 19 to 23 percent $GM_1$, about 36 to 44 percent $GD_{1a}$, about 14 to 18 percent $GD_{1b}$ and about 17 to 21 percent $GT_{1b}$.

3. A method as in claim 2, wherein said composition comprises, by weight, about 21 percent $GM_1$, about 40 percent $GD_{1a}$, about 16 percent $GD_{1b}$ and about 19 percent $GT_{1b}$.

4. A method as in claim 1, wherein said composition comprises at least two of said gangliosides.

5. A method as in claim 1, wherein said composition comprises at least three of said gangliosides.

6. A method for treating pain due to peripheral neuropathies comprising administering to a host in pain a composition comprising an effective pain relieving amount of at least one ganglioside selected from the group consisting of $GM_1$, $GD_{1a}$, $GD_{1b}$ and $GT_{1b}$.

7. A method as in claim 6, wherein said composition comprises, by weight, about 19 to 23 percent $GM_1$, about 36 to 44 percent $GD_{1a}$, about 14 to 18 percent $GD_{1b}$, and about 17 to 21 percent $GT_{1b}$.

8. A method as in claim 6, wherein said composition comprises, by weight, about 21 percent $GM_1$, about 40 percent $GD_{1a}$, about 16 percent $GD_{1b}$ and about 19 percent $GT_{1b}$.

9. A method as in claim 6, wherein said composition comprises at least two of said gangliosides.

10. A method as in claim 6, wherein said composition comprises at least two of said gangliosides.

* * * * *